United States Patent [19]

Fuji et al.

[11] Patent Number: 5,106,970
[45] Date of Patent: Apr. 21, 1992

[54] OPTICALLY ACTIVE 4-MORPHOLINO-2-(1-NAPHTHYLME-THYL)-4-OXOBUTYRIC ACID 2'-HYDROXY-1,1'BINAPHTHALEN-2-YL

[75] Inventors: Kaoru Fuji, Kyoto; Manabu Node, Osaka; Fujie Tanaka, Kyoto, all of Japan

[73] Assignee: Takasago International Corporation, Tokyo, Japan

[21] Appl. No.: 724,628

[22] Filed: Jul. 2, 1991

[30] Foreign Application Priority Data

Jul. 6, 1990 [JP] Japan .................. 2-177296

[51] Int. Cl.$^5$ .......................... C07D 295/192
[52] U.S. Cl. .......................... 544/171
[58] Field of Search .......................... 544/171

[56] References Cited
U.S. PATENT DOCUMENTS 4,656,269  4/1987  Iizuka et al. .......... 548/344

*Primary Examiner*—Robert W. Ramsuer
*Attorney, Agent, or Firm*—Sughrue, Mion, Zinn, Macpeak & Seas

[57] ABSTRACT

Optically active 4-morpholino-2-(1-naphthylmethyl)-4-oxobutyric acid 2'-hydroxy-1,1'-binaphthalen-2-yl represented by formula (I):

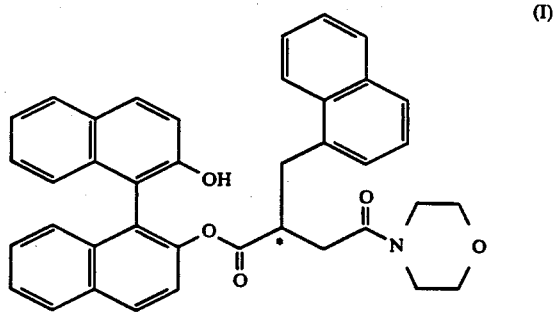

(I)

wherein * indicates an asymmetric carbon atom, which is prepared by reacting 4-morpholino-4-oxobutyric acid 2'-hydroxy-1,1'-binaphthalen-2-yl represented by formula (II):

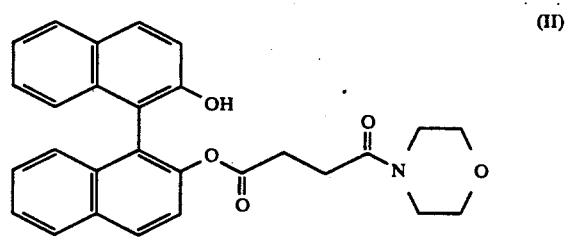

(II)

with a 1-halomethylnaphthalene in the presence of a base. The compound (I) is a useful intermediate for preparing pharmaceuticals such as a renin inhibitors.

2 Claims, No Drawings

OPTICALLY ACTIVE 4-MORPHOLINO-2-(1-NAPHTHYLMETHYL)-4-OXOBUTYRIC ACID 2'-HYDROXY-1,1'BINAPHTHALEN-2-YL

FIELD OF THE INVENTION

The invention relates to optically active 4-morpholino-2-(1-naphthylmethyl)-4-oxobutyric acid 2'-hydroxy-1,1'-binaphthalen-2-yl which is useful as a starting material for preparing antihypertensive agents based on human renin inhibitory activity and to a process for preparing the same.

BACKGROUND OF THE INVENTION

Known compounds useful as antihypertensive agents for their human renin inhibitory activity include, for example, a compound represented by formula (III):

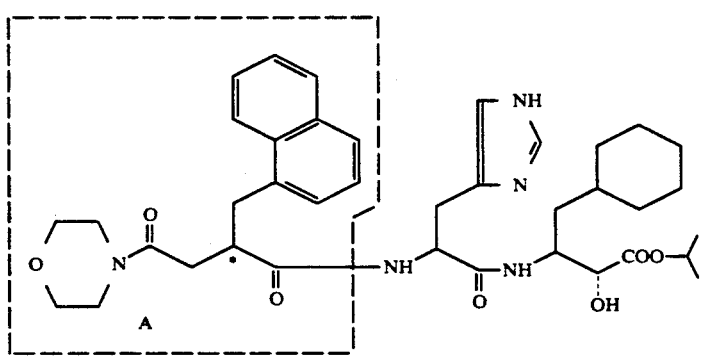

(III)

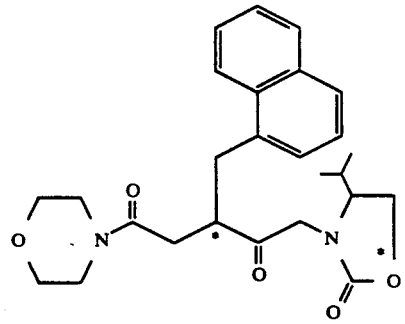

(IV)

For details, Chem. Pharm. Bull., Vol. 38, p. 103 (1990) can be referred to. For practical application, however, this process needs an improvement in view of the insufficient yield of the alkylation.

wherein * indicates an asymmetric carbon atom.

Of the optical isomers of formula (III) assigned to the asymmetric carbon atom marked with * in the unit A, the one having an (R)-configuration exhibits higher activity. Therefore, it is important in the synthesis of the compound (III) to start with a compound having an asymmetric carbon atom at the position corresponding to the mark *, and it is necessary to prepare such an intermediate through asymmetric synthesis.

A known process for preparing such an intermediate having controlled asymmetry at the position * comprises acylating a lithium salt of optically active oxazolidinone with an acyl halide, diastereo-selectively alkylating the acylated compound with benzyl bromoacetate in the presence of lithium diisopropylamide (LDA), debenzylating the alkylated compound with palladium-on-carbon, and condensing the resulting compound with morpholine in the presence of diethylphosphoryl cyanide (DEPC) and triethylamine to obtain a compound represented by formula (IV):

JP-A-2-157243 (the term "JP-A" as used herein means an "unexamined published Japanese patent application") teaches a process for preparing a compound represented by formula (V):

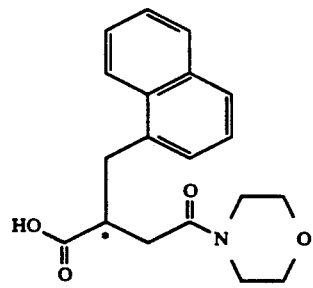

(V)

by asymmetrically hydrogenating 2-(1-naphthylmethylidene)-succinic acid in the presence of a rhodium complex catalyst to obtain optically active (R)-2-(1-naphthylmethyl)succinic acid and introducing a morpholino group thereinto. However, the introduction of a morpholino group involves many reaction steps, still needing a further improvement for practical application.

Accordingly, an intermediate which can easily introduce the asymmetric moiety marked * in the unit A of the compound of formula (III) as well as a means for synthesizing the same have been keenly demanded.

SUMMARY OF THE INVENTION

In the light of the above-described present situation, the inventors have conducted extensive investigations and, as a result, found that optically active 4-morpholino-2-(1-naphthylmethyl)-4-oxobutyric acid 2'-hydroxy-1,1'-binaphthalen-2-yl represented by formula (I):

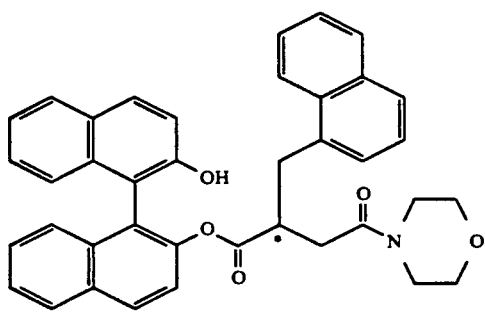

wherein * indicates an asymmetric carbon atom, which can easily be obtained by enantioselective alkylation of an optically active binaphthol derivative, 4-morpholino-4-oxobutyric acid 2'-hydroxy-1,1'-binaphthalen-2-yl, represented by formula (II):

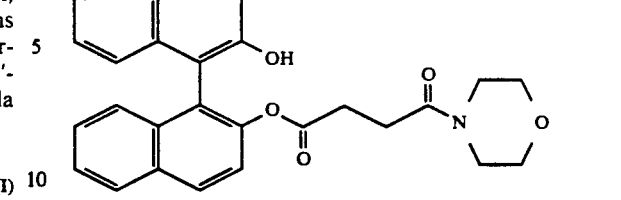

with a 1-halomethylnaphthalene in the presence of a base satisfies requirements as an intermediate for synthesizing, for example, the compound of formula (III). The present invention has been completed based on this finding.

Thus, the present invention provides optically active 4-morpholino-2-(1-naphthylmethyl)-4-oxobutyric acid 2'-hydroxy-1,1'-binaphthalen-2-yl represented by formula (I) which is useful as an intermediate for preparing pharmaceuticals and a process for preparing the same.

DETAILED DESCRIPTION OF THE INVENTION

The compound of formula (I) according to the present invention can be prepared according to reaction scheme A.

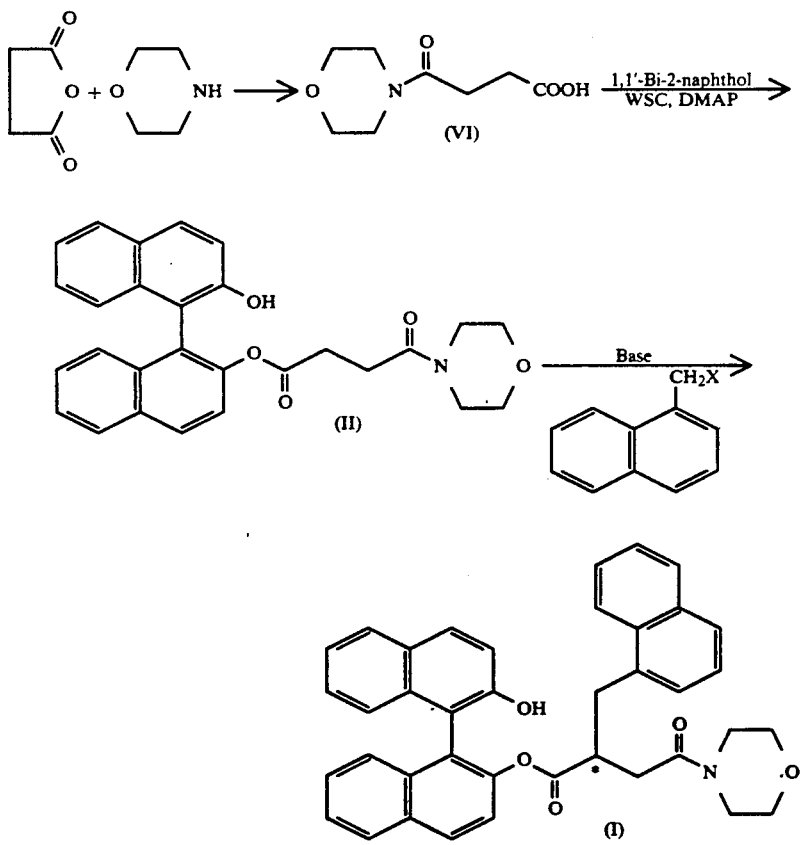

wherein X represents a halogen atom; WSC represents 1-ethyl-3-(3-dimethylaminopropyl)carbodiimide hydrochloride; DMAP represents 4-dimethylaminopyridine; THF represents tetrahydrofuran; and HMPA represents hexamethylphosphoramide.

That is, the desired compound (I) can be obtained in a simple manner by a process comprising direct enantioselective alkylation of an optically active 1,1'-bi-2-naphthol ester.

4-Morpholino-4-oxobutyric acid of formula (VI) can be obtained by reacting succinic anhydride and morpholine in THF at room temperature under a nitrogen atmosphere.

The optically active 4-morpholino-4-oxobutyric acid 2'-hydroxy-1,1'-binaphthalen-2-yl of formula (II), which is a novel compound, can be obtained by reacting the compound of formula (VI) and optically active 1,1'-bi-2-naphthol in methylene chloride in the presence of WSC and DMAP under a nitrogen atmosphere at room temperature for 20 to 26 hours while stirring.

The optically active 1,1'-bi-2-naphthol which can be used in the process is commercially available, or it is synthesized by, for example, optical resolution of racemic 1,1'-bi-2-naphthol according to the process described in JP-A-61-204138 or JP-A-63-148996 into the (R)-compound and (S)-compound, the racemic 1,1'-bi-2-naphthol used here being obtained by reacting anhydrous ferric chloride with a 2-naphthol derivative as described, e.g., in JP-A-61-172841.

Where racemic 1,1'-bi-2-naphthol is used in the process in place of optically active 1,1'-bi-2-naphthol, there is obtained a racemate of 4-morpholino-4-oxobutyric acid 2'-hydroxy-1,1'-binaphthalen-2-yl.

The desired optically active 4-morpholino-2-(1-naphthylmethyl)-4-oxobutyric acid 2'-hydroxy-1,1'-binaphthalen-2-yl of formula (I) can be obtained by reacting the compound of formula (II) with a 1-halomethylnaphthalene in an ether solvent, e.g., THF-HMPA, and diethyl ether-HMPA, in the presence of a base under a nitrogen atmosphere at a temperature of from −78° to −45° C. for a period of form 1 to 2 hours while stirring.

The halogen in the 1-halomethylnaphthalene is preferably bromine. Bases which can be used in the reaction include those capable of forming an enolate at the α-position of the ester, with so-called amide bases, e.g., LDA and lithium-2,2,6,6-tetramethylpiperazide, being particularly preferred.

Thus, optically active 4-morpholino-2-(1-naphthylmethyl)-4-oxobutyric acid 2'-hydroxy-1,1'-binaphthalen-2-yl of formula (I) can be synthesized through simple steps by making use of enantioselective alkylation of a binaphthyl ester.

As illustrated in the following reaction scheme B, the thus obtained compound of formula (I) is hydrolyzed with lithium hydroxide, potassium hydroxide, etc. to obtain a carboxylic acid, which is then linked with an amine through a peptide linkage in a usual manner, thereby to provide a compound having introduced thereinto a unit A important for manifestation of renin inhibitory activity. Accordingly, the compound of formula (I) is an industrially excellent substance which can be made use of in syntheses of pharmaceuticals such as various renin inhibitors including the compound of formula (III).

Reaction Scheme B:

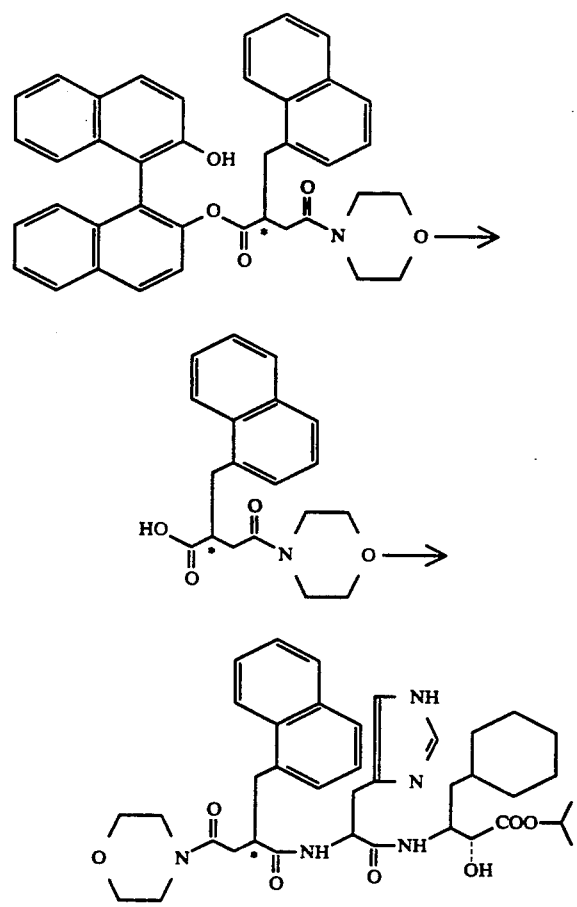

Renin inhibitors which can be synthesized with more ease by starting with the compound of formula (I) according to the present invention include the compounds described in Chem. Pharm. Bull. (Japan), Vol. 38, p. 103 (1990), Drugs Fut., Vol. 13, p. 1042 (1988), and JP-A-1-172374 as well as the compound of formula (III).

Besides, the process according to the present invention makes it possible to prepare the compound of formula (I), i.e., a useful intermediate for pharmaceuticals, in good yield and satisfactory optical yield while involving a short reaction route and is therefore of high industrial significance.

The present invention is now illustrated in greater detail with reference to Examples, but it should be understood that the present invention is not deemed to be limited thereto. All the percents are by weight unless otherwise indicated.

EXAMPLE 1

Synthesis, of 4-Morpholino-4-oxobutyric Acid 2'-Hydroxy-1,1'-binaphthalen-2-yl

In 10 ml of THF was dissolved 1.814 g (81.3 mmole) of succinic anhydride, and 7.04 ml (81.3 mmole) of morpholine was added dropwise thereto from a syringe at room temperature under a nitrogen atmosphere. After stirring the reaction mixture for 1 hour, the precipitated crystals were collected by filtration and washed with a 1:2 (by volume) mixture of ethyl acetate and hexane to obtain 14.3 g (percent yield: 94%) of crude crystals of 4-morpholino-4-oxobutyric acid.

In 150 ml of methylene chloride were dissolved 1.58 g (1.2 equiv.) of the resulting 4-morpholino-4-oxobutyric acid, 2.00 g (1 equiv.) of (R)-(+)-1,1'-bi-2-naphthol, and 91.0 mg (0.1 equiv.) of DMAP, and 2.04 g (1.5 equiv.) of WSC was added to the solution at room temperature under a nitrogen atmosphere, followed by stirring for 25 hours. The resulting solution was added to a 5% hydrochloric acid aqueous solution and then extracted with methylene chloride. The extract was washed with a sodium chloride aqueous solution and dried over anhydrous magnesium sulfate, and the solvent was removed by distillation. The residue was purified by silica gel flash column chromatography using ethyl acetate to obtain 2.43 g (percent yield: 76%) of 4-morpholino-4-oxobutyric acid 2'-hydroxy-1,1'-binaphthalen-2-yl. Crystallization from a mixed solvent of methylene chloride and diethyl ether yielded crystals of 4-morpholino-4-oxobutyric acid 2'-hydroxy-1,1'-binaphthalen-2-yl.

$[\alpha]_D^{24.0} = +77.5°$ (c=1.0, CHCl$_3$)

$^1$H-NMR (200 MHz, CDCl$_3$, δ): 2.10 (t, 2 H, J=7.2 Hz), 2.34–2.61 (m, 2 H), 3.11–3.16 (m, 2 H), 3.50–3.64 (m, 6 H), 5.44 (s, 1 H), 7.04–8.10 (m, 12 H)

IR (CHCl$_3$, cm$^{-1}$): 3530, 3010, 1750, 1640

MS (m/e): 455, 286, 170

High MS for C$_{28}$H$_{25}$NO$_5$:
Calcd.: 455.173
Found: 455.172

EXAMPLE 2

Synthesis of (2R)-4-Morpholino-2-,(1-naphthylmethyl)-4-oxobutyric Acid 2'-Hydroxy-1,1'-binaphthalen-2-yl A solution of 453.2 mg (0.995 mmole, 1 equiv.) of 4-morpholino-4-oxobutyric acid 2'-hydroxy-1,1'-binaphthalen-2-yl obtained in Example 1 in 7.0 ml of THF was added dropwise to a solution of 2.09 mmole (2.1 equiv.) of LDA in 5.0 ml of THF and 1.64 ml (9.9 mmole, 10 equiv.) of HMPA at −78° C. under a nitrogen atmosphere with stirring. After stirring for 1 hour, a solution of 485.2 mg (2.19 mmole, 2.2 equiv.) of 1-bromomethylnaphthalene in 3.0 ml of THF was added to the solution by a syringe, followed by stirring at −78° C. for 1 hour and then at −45° C. for 2 hours. The resulting solution was added to a 1% hydrochloric acid aqueous solution and extracted with diethyl ether. The extract was washed successively with water and a sodium chloride aqueous solution and dried over anhydrous magnesium sulfate, and the solvent was removed by distillation. A part of the residue was subjected to fractional thin layer chromatography using a 1:1 (by volume) mixture of ethyl acetate and hexane to obtain 16.1 mg of a diastereomer mixture of 4-morpholino-2-(1-naphthylmethyl)-4-oxobutyric acid 2'-hydroxy-1,1'-binaphthalen-2-yl. The RR:RS diastereomer ratio was found to be 85:15 by $^1$H-NMR (400 MHz). The rest of the above residue was subjected to silica gel flash column chromatography (ethyl acetate:hexane =3:2→4:1 by volume) to obtain 465.7 mg of a diastereomer mixture of 4-morpholino-2-(1-naphthylmethyl)-4-oxobutyric acid 2'-hydroxy-1,1'-binaphthalen-2-yl (total yield: 481.8 mg, percent yield: 81%). Crystallization of the combined product with a mixed solvent of methylene chloride and diethyl ether gave crystals of an (R,R)-diastereomer of 4-morpholino-2-(1-naphthylmethyl)-4-oxobutyric acid 2'-hydroxy-1,1'-binaphthalen-2-yl.

(R,R)-Compound:

$[\alpha]_D^{24.0} = +53.9°$ (c=1.0, CHCl$_3$)

$^1$H-NMR (400 MHz, CDCl$_3$, δ): 2.01 (dd, 1 H, J=6.0, 16.3 Hz, —CH$_2$Ar), 2.10 (dd, 1 H, J=7.9, 16.3 Hz, —CH$_2$AR), 2.56 (dd, 1 H, J=9.2, 13.9 Hz, —CH$_2$CO—), 2.86 (dd, 1 H, J=5.9, 13.9 Hz, —CH$_2$CO—), 3.04 (m, 2 H), 3.19 (m, 1 H), 3.39–3.51 (m, 6 H, morpholine—CH$_2$—), 5.46 (s, 1 H, —OH—), 7.07–8.06 (m, 19 H, ArH)

IR (CHCl$_3$, cm$^{-1}$): 3540, 3010, 1750, 1640

MS (m/e): 595, 310, 286

High MS for C$_{39}$H$_{33}$NO$_5$:
Calcd.: 595.236
Found: 595.235

(R,S)-Compound:

$^1$H-NMR (400 MHz, CDCl$_3$, δ): 2.04 (dd, 1 H, J=4.6, 16.3 Hz), 2.39–2.54 (m, 3 H), 3.03–3.19 (m, 3 H), 3.35–3.81 (m, 6 H), 5.29 (s, 1 H), 7.05–8.11 (m, 19 H)

IR (CHCl$_3$, cm$^{-1}$): 3540, 3010, 1750, 1640

While the invention has been described in detail and with reference to specific examples thereof, it will be apparent to one skilled in the art that various changes and modifications can be made therein without departing from the spirit and scope thereof.

What is claimed is:

1. Optically active 4-morpholino-2-(1-naphthylmethyl)-4-oxobutyric acid 2'-hydroxy-1,1'-binaphthalen-2-yl represented by formula (I):

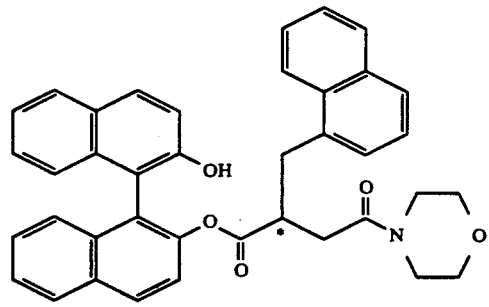

(I)

wherein * indicates an asymmetric carbon atom.

2. 4-Morpholino-4-oxobutyric acid 2'-hydroxy-1,1'-binaphthalen-2-yl represented by formula (II):

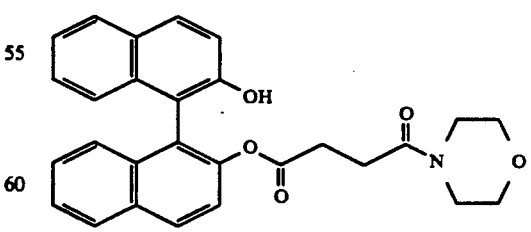

(II)

* * * * *